United States Patent [19]

Lubisch et al.

[11] Patent Number: 5,260,318
[45] Date of Patent: Nov. 9, 1993

[54] PHENYLPIPERIDYLAMINES AND DRUGS CONTAINING THEM

[75] Inventors: Wilfried Lubisch, Mannheim; Sabine Schult, Heidelberg; Rudolf Binder, Worms; Manfred Raschack, Weisenheim am Sand; Roland Reinhardt, Kaiserslautern; Dietmar Seemann, Nussloch, all of Fed. Rep. of Germany

[73] Assignee: BASF Aktiengesellschaft, Ludwigshafen, Fed. Rep. of Germany

[21] Appl. No.: 760,159

[22] Filed: Sep. 16, 1991

[30] Foreign Application Priority Data

Oct. 16, 1990 [DE] Fed. Rep. of Germany ....... 4032766

[51] Int. Cl.$^5$ ................. A61K 31/445; C07D 401/12; C07D 211/56
[52] U.S. Cl. .................... 514/318; 514/329; 546/194; 546/223
[58] Field of Search ............. 546/193, 194, 208, 223; 514/318, 329

[56] References Cited

U.S. PATENT DOCUMENTS

| | | | |
|---|---|---|---|
| 3,468,892 | 9/1969 | Tomcuycik | 546/223 |
| 4,198,411 | 4/1980 | Sanczuk et al. | 544/333 |
| 4,603,138 | 7/1986 | Maschler | 546/223 |
| 4,835,165 | 5/1989 | Cross | 546/194 |
| 4,902,800 | 2/1990 | Skotnicki | 546/208 |

FOREIGN PATENT DOCUMENTS

| | | |
|---|---|---|
| 0369627 | 5/1990 | European Pat. Off. . |
| 749887 | 5/1943 | Fed. Rep. of Germany . |
| 1052302 | 4/1964 | United Kingdom ............... 546/208 |

OTHER PUBLICATIONS

Berichte Der Deutschen Chemischen Gesellschaft, 74, 1941, pp. 1648–1667, E. Cerkovnikov, et al., "Uber Eine Neue Reihe".
Helvetica Chimica Acta, vol. 26, 1943, pp. 1132–1142, V. Hahn, et al., "Uber Substituierte 4-Amino-Piperidine".

Primary Examiner—C. Warren Ivy
Assistant Examiner—Celia Chang
Attorney, Agent, or Firm—Oblon, Spivak, McClelland, Maier & Neustadt

[57] ABSTRACT

Phenylpiperidylamines of the formula I

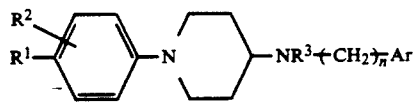

$R^1$ is H, $NO_2$, $R^4SO_2NH$,

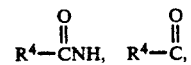

N≡C, $CF_3$, $CF_3O$, F, Cl, Br, $C_1$-$C_4$-alkyl, $R^3O$, $CO_2R^3$, CHO, CH=$NOR^3$, $CH_3OR^3$ and
$R^2$ is H, F, Cl, Br, $C_1$-$C_4$-alkyl or $R^4O$, where $R^1$ and $R^2$ are not both H,
$R^3$ is H or $R^4$,
$R^4$ is $C_1$-$C_4$-alkyl or phenyl,
n is 1, 2, 3 or 4 and
Ar is

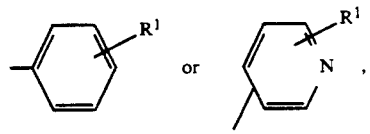

and the physiologically tolerated salts thereof, are used as active ingredients in drugs.

2 Claims, No Drawings

PHENYLPIPERIDYLAMINES AND DRUGS CONTAINING THEM

The present invention relates to novel substituted phenylpiperidylamines, the pharmaceutically utilizable salts thereof and pharmaceutical formulations which contain them as active ingredient.

Phenylpiperidylamines are described in BE 678 063 (antiproteolytic action) and U.S. Pat. No. 4,902,800 (interleukin-I inhibitor). In addition, phenylpiperidylamines with an antihistamine action have been described in DRP 749887 (1941); E. Cerkovnikov et al., Chem. Ber. 74 (1941) 1648, 1658 and 1661 and V. Hahn et al., Helv. Chim. Acta 26 (1943) 1132.

It is an object of the present invention to develop novel antiarrhythmics of Vaughan-Williams class III (see "Mechanisms and treatment of cardiac arrhythmias", ed. H. J. Reiser and L. N. Horowitz, published by Urban and Schwarzenberg, Baltimore and Munich, 1985, chapter II.C) with improved properties.

We have found that this object is achieved by phenylpiperidylamines of the formula I

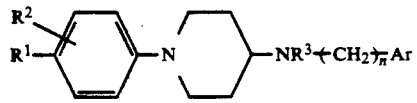

$R^1$ is H, $NO_2$, $R^4SO_2NH$,

N=C, $CF_3$, $CF_3O$, F, Cl, Br, $C_1$-$C_4$-alkyl, $R^3O$, $CO_2R^3$, CHO, $CH=NOR^3$, $CH_3OR^3$ and $R^2$ is H, F, Cl, Br, $C_1$-$C_4$-alkyl or $R^4O$, where $R^1$ and $R^2$ are not both H, $R^3$ is H or $R^4$, $R^4$ is $C_1$-$C_4$-alkyl or phenyl, n is 1, 2, 3 or 4 and Ar is

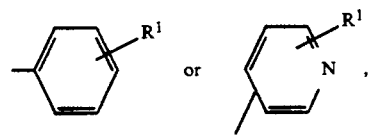

and the physiologically tolerated salts thereof.

The novel compounds can e prepared by various processes similar to those which have been disclosed:

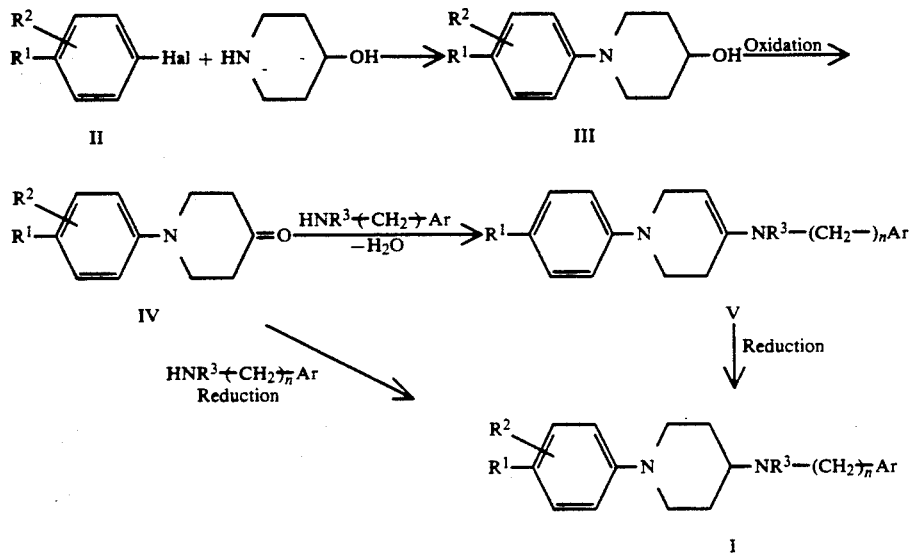

The route shown in scheme 1 is based on a method described by Taylor and Skotwicki for preparing derivatives of compounds IV (Synthesis (1981) 606). Starting from the aromatic halide II (Hal=F, Cl, Br) in which $R^1$ is an electron-attracting group, reaction with 4-piperidinol in preferably polar solvents, such as dimethylformamide, alcohols and ketones, at elevated temperature, mainly from 60° to 150° C., in the presence of bases, such as potassium carbonate, results in the aniline derivative III. If $R^1$ is not an electron-attracting group, the reaction is carried out at elevated temperature, mainly above 100° C., with metal or metal salt catalysis, employing copper salts or copper powder in particular. Oxidation to IV is preferably carried out by the Pfitzner-Moffat method (dicyclohexylurea/dimethyl sulfoxide) or Swern method (oxalyl chloride or trifluoroacetic anhydride/dimethyl sulfoxide). The novel amine I is obtained by reductive amination of IV, which is mainly carried out at room temperature in the presence of reducing agents such as sodium cyanoborohydride or hydrogen on, for example, Pd/carbon, Pt/carbon or Raney nickel in polar solvents such as alcohols. An alternative possibility is to prepare the enamine V from IV and the amine $HNR^3$-$(CH_2)$—$_n$Ar in a conventional manner (aprotic solvent, preferably toluene; acid catalysis, preferably p-toluenesulfoic acid and formic acid, elevated temperature) and then reduce this in, mainly, alcohols with reducing agents such as sodium borohydride or hydrogen on the conventional metal catalysts such as Pd/carbon or Pt/carbon to give the product I.

Scheme 2:

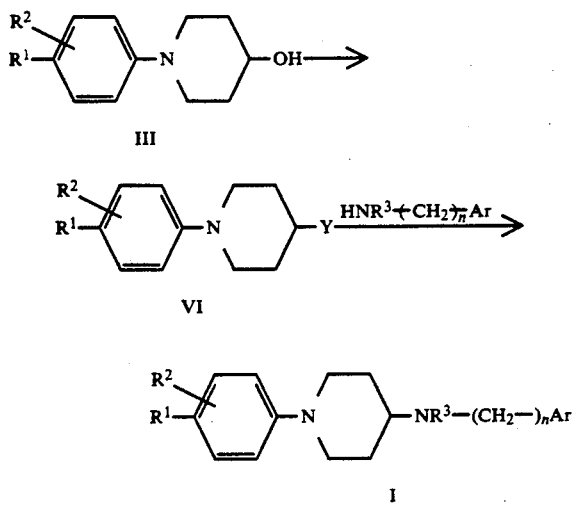

In scheme 2, the alcohol II is converted into VI, where Y is a leaving group such as chlorine or bromine (which can be introduced in a conventional manner from III by reaction with thionyl chloride or phosphorus tribromide), or OSO$_2$CF$_3$ or OSO$_2$ (which can be introduced by reacting III with the appropriate sulfonyl chlorides or anhydrides). The reaction of VI with the amine HNR$^3$—(CH$_2$)—$_n$Ar to give I is carried out with or without solvents at from 25° to 150° C., in the presence or absence of a base.

Scheme 3:

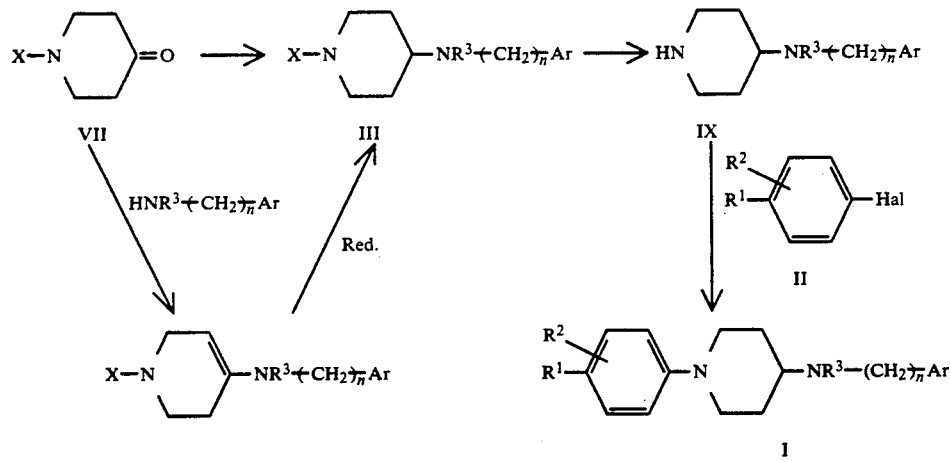

In variant 3 (scheme 3), the product is obtained by reacting the amine IX with the halide II in a manner similar to that in scheme 1. Starting from the piperidone VII where x is a protective group such as benzyl,

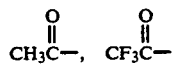

or tert-butoxycarbonyl (BOC), VIII is produced by reductive amination with the amine HNR$^3$—(CH$_2$)—$_n$Ar. This is carried out in solvents such as alcohols and using reducing agents such as sodium cyanoborohydride or hydrogen on Pd/carbon, Pt/carbon or Raney nickel. Elimination of the protective group X, either catalytically with hydrogen or hydrolytically with HCl or NaOH, results in the amine IX. An alternative possibility is to prepare an enamine from VII and the amine HNR$^3$—(CH$_2$)—$_n$Ar in a conventional manner (aprotic solvent, preferably toluene; acid catalysis, preferably p-toluenesulfonic acid and formic acid; elevated temperature) and then reduce it in, mainly, alcohols with reducing agents such as sodium borohydride or hydrogen on the conventional metal catalysts such as Pd/carbon or Pt/carbon to give the product VIII.

Scheme 4:

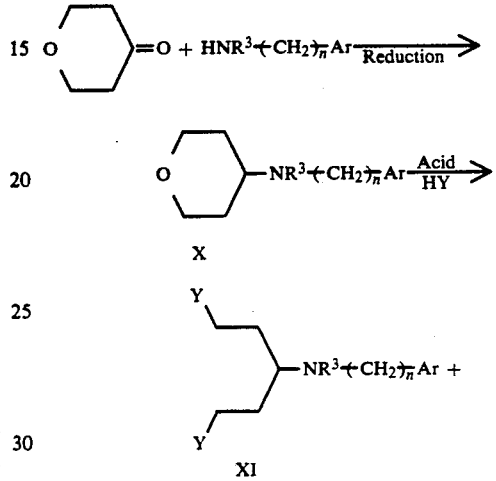

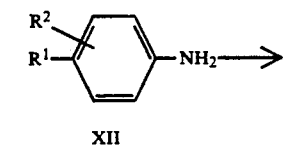

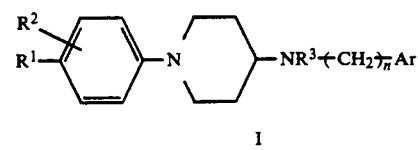

Another preparation starts from tetrahydro-4-pyranone (scheme 4) which is converted into X by reductive amination in a conventional manner similar to the preparation of VIII in scheme 3. X is converted into the dihalide XI (Y=halogen) in a concentrated acid such as hydrobromic acid or hydrochloric acid, with or without solvent, at elevated temperature. The aniline XII is alkylated with XI in polar solvents such as alcohols and dimethylformamide or without solvent at elevated temperature, in the presence or absence of a base such as potassium carbonate.

The phenylpiperidylamines obtained in this way can, if required, be converted into the acid addition salt of a physiologically tolerated acid. A list of conventional physiologically tolerated acids is to be found in Fortschritte der Arzneimittelforschung, 1966, Birkhäuser Verlag, vol. 10, 224–285, Germany, Switzerland.

The acid addition salts are usually obtained in a conventional manner by mixing the free base or solution thereof with the appropriate acid or solution thereof in an organic solvent, eg. a lower alcohol such as methanol, ethanol or propanol, or a lower ketone such as acetone, methyl ethyl ketone or methyl isobutyl ketone, or an ether such as diethyl ether, tetrahydrofuran or dioxane. To improve crystallization it is possible to use mixtures of the said solvents. In addition, pharmaceutically acceptable aqueous solutions of acid addition compounds of the phenylpiperidylamines of the formula I can be prepared by dissolving the free base in an aqueous acid solution.

The novel phenylpiperidylamines are class III antiarrhythmics. In addition, they have affinity for the sigma receptor and therefore have antipsychotic, anti-convulsant and neuroprotective actions. We have also found that the compounds block the ATP-sensitive K channel.

The present invention therefore also relates to therapeutic agents for topical and, especially, systemic administration which contain a compound of the formula I as active ingredient in addition to conventional carriers and/or other pharmaceutical inactive ingredients.

The therapeutic agents or compositions are prepared using the conventional liquid or solid carriers or diluents and the inactive ingredients conventionally used in pharmaceutical technology, appropriate for the required mode of administration and with a suitable dosage, in a conventional manner, for example by mixing the active ingredient with the solid and liquid carriers and inactive ingredients conventional in such products.

The agents can be administered orally, parenterally or topically. Examples of suitable compositions are uncoated or (film-)coated tablets, capsules, pills, powders, solutions or suspensions, solutions for infusion or injection, and pastes, ointments, gels, creams, lotions, dusting powders, solutions or emulsions and sprays.

The therapeutic agents can contain the compounds to be used according to the invention in a concentration of from 0.01 to 1% for local administration and preferably in a single dose of from 0.1 to 25 mg per kg of body weight for systemic administration, and can be administered in one or more doses each day depending on the nature and severity of the disorders.

Examples of inactive ingredients which are conventionally used in pharmaceutical technology are, for local administration, alcohols such as ethanol, isopropanol, ethoxylated castor oil or ethoxylated hydrogenated castor oil, polyacrylic acid, glycerol monostearate, liquid paraffin, petrolatum, lanolin, polyethylene glycol, polypropylene glycol, stearate and ethoxylated fatty alcohol and, for systemic administration, lactose, propylene glycol and ethanol, starch, talc or polyvinylpyrrolidone. The products can also contain an anti-oxidant, for example tocopherol or butylated hydroxyanisole or butylated hydroxytoluene, or flavor improvers, stabilizers, emulsifiers, bleaches etc. It is necessary that all the substances used in the preparation of pharmaceutical compositions are toxicologically innocuous and compatible with the active ingredients used. Preparation of starting materials and intermediates:

PREPARATION 1

1.0 g (4.5 mmol) of 1-(4-nitrophenyl)-4-hydroxypiperidine are hydrogenated in a conventional manner with Pd/carbon in methanol. 0.8 g of 1-(4-aminophenyl)-4-hydroxypiperidine is obtained. Melting point 176° C.

PREPARATION 2

20 g (0.10 mol) of the product from Preparation 1 and 10.5 g (0.10 mol) of triethylamine are dissolved in methylene chloride and, at 0° C., 9.0 g (0.11 mol) of acetyl chloride dissolved in methylene chloride are added dropwise. The mixture is stirred at 0° C. for 3 h and then poured into water. The aqueous phase is saturated with sodium chloride, when the product precipitates. 18.6 g of 1-(4-acetaminophenyl)-4-hydroxypiperidine are obtained. Melting point 191° C.

PREPARATION 3

18.0 g (76.8 mmol) of the product from Preparation 2 are dissolved in 300 ml of dimethyl sulfoxide/toluene (1:2) and, successively, 6.2 ml (76.8 mmol) of pyridine, 50.0 g (240 mmol) of dicyclohexylcarbodiimide and, at 0° C., dropwise 3.0 ml (38.4 mmol) of trifluoroacetic acid are added. The mixture is stirred at room temperature for 16 h and then poured into water and extracted with ethyl acetate. The organic phase is dried and concentrated under reduced pressure. The residue is purified by chromatography (eluent: toluene/acetone 1:1). 13.2 g of 1-(4-acetaminophenyl)-4-piperidone are obtained Melting point 158-159° C.

PREPARATION 4

The product from Preparation 1 is reacted with methanesulfonyl chloride in tetrahydrofuran in a similar manner to Example 9. 1-(4-Methanesulfonylaminophenyl)-4-hydroxypiperidine is obtained. Melting point 126°–129° C.

PREPARATION 5

The product from Preparation 4 is reacted with dicyclohexylcarbodiimide/DMSO in a similar manner to Preparation 3. 1-(4-Methanesulfonylaminophenyl)-4-piperidone is obtained.

PREPARATION 6

17.8 g (63 mmol) of titanium tetraisopropylate were added dropwise to 7.1 g (50 mmol) of N-acetylpiperidine and 6.1 g (50 mmol) of N,N-benzylmethylamine at 25° C. The viscous mass resulting after stirring for one hour was taken up in 50 ml of ethanol and then 2.1 g (30 mmol) of sodium cyanoborohydride were added a little at a time. The mixture was left to stir at room temperature for 20 hours. Then 10 ml of water were added dropwise, the inorganic precipitate was filtered off, and the filtrate was concentrated under reduced pressure. The resulting residue was partitioned between ethyl acetate and water, and the organic phase was separated off, dried and again concentrated under reduced pressure. 10.0 g of 1-acetyl-4-(N,N-benzylmethylamino)-piperidine of melting point 44°–45° C. were obtained.

PREPARATION 7

9.5 g (38.4 mmol) of the product from Preparation 6 were dissolved in 200 ml of ethanol/4M sodium hydroxide solution (1:1) and refluxed for 10 hours. The ethanol was then removed under reduced pressure, the residue was diluted with water, and the mixture was extracted with ethyl acetate. The organic phase was dried and evaporated in a rotary evaporator. 6.5 g of 4-(N,N-benzylmethylamino)piperidine were obtained as an oil.

$^1$H NMR (CDCl$_3$): δ = 1.4–1.6 (2H), 1.7–1.9 (3H), 2.1 (3H), 2.5–2.7 (3H), 3.05 (2H), 3.55 (2H) and 7.15–7.3 (5H) ppm.

PREPARATION 8

28.4 g (0.15 mol) of N-benzyl-4-piperidone, 20.3 g (0.15 mol) of N-methyl-N-(2-phenylethyl)amine and 5 ml of formic acid in 250 ml of toluene were refluxed with a water trap until no more water was evolved. The mixture was then evaporated in a rotary evaporator, and the resulting 1-benzyl-4-(N-methyl-N-(2-phenylethyl)amino)-1,2,5,6-tetrahydropyridine was immediately reacted further as crude product.

For this, it was dissolved in 500 ml of ethanol and, at 10° C., 17.0 g (0.45 mol) of sodium borohydride were added a little at a time. The mixture was stirred at room temperature for 16 hours and then evaporated in a rotary evaporator, and the residue was partitioned between methylene chloride and water. The organic phase was dried and evaporated in a rotary evaporator. The resulting oil was crystallized as the dioxalate. 57.4 g of 1-benzyl-4-(N-methyl-N-(2-phenylethyl)amino)-piperidine dioxalate were obtained. Melting point 203°–204° C. (i-propanol).

PREPARATION 9

32.8 g (0.1 mol) of the product from Preparation 8 were dissolved in 500 ml of methanol and, after addition of 5 g of palladium/carbon (10%), hydrogenated. The mixture was then filtered and the filtrate was evaporated in a rotary evaporator. The resulting oil crystallized as the dioxalate. 35.8 g of 4-(N-methyl-N-(2-phenylethyl)amino)piperidine dioxalate were obtained. Melting point 169°–170° C.

PREPARATION 10

17.1 g (0.14 mol) of N-acetyl-4-piperidone and 16.9 g (0.14 mol) of N-(4-fluorobenzyl)-N-methylamine were reacted in a similar manner to Preparation 6. 25.1 g of 1-acetyl-4-(N-(4-fluorobenzyl)-N-methylamino)piperidine were obtained.

$^1$H NMR (CDCl$_3$): δ = 1.4–1.6 (2H), 1.75–1.9 (2H), 2.1 (3H), 2.2 (3H), 2.4–2.7 (2H), 3.0 (1H), 3.5 (2H), 3.9 (1H), 4.7 (1H), 7.0 (2H) and 7.25 (2H) ppm.

PREPARATION 11

26.5 g (0.10 mol) of the product from Preparation 10 were hydrolyzed in a similar manner to Preparation 7. 19.7 g of 4-(N-(4-fluorobenzyl)-N-methylamino)piperidine were obtained as an oil.

$^1$H NMR (CDCl$_3$): δ = 1.4–1.6 (2H), 1.8–1.9 (2H), 2.1 (3H), 2.4–2.7 (4H), 3.2 (2H), 6.9–7.05 (2H) and 7.2–7.3 (2H) ppm.

PREPARATION 12

1.8 g (4.7 mmol) of the product from Example 40 were dissolved in 100 ml of methanol and hydrogenated in the presence of 0.3 g of palladium/active carbon (10%). The mixture was then filtered and the filtrate was evaporated in a rotary evaporator. 1.3 g of 1-(4-aminophenyl)-4-(N-(2-(4-aminophenyl)ethyl)-N-methylamino)piperidine were obtained as an oil.

$^1$H NMR (d$_6$-DMSO): δ = 1.4–1.6 (2H), 1.7–1.8 (2H), 2.1 (3H), 2.3–2.7 (7H), 3.4 (2H), 4.0–4.6 (4H), 6.4 (4H), 6.7 (2H) and 6.85 (2H) ppm.

PREPARATION 13

1.5 g (4.0 mmol) of the amine from Example 36 were suspended in 100 ml of ethanol, and a solution of 0.26 g of copper(II) sulfate pentahydrate in 0.5 ml of water was added. Then 2 g of sodium borohydride were added in portions and the mixture was gently refluxed for 2 hours. It was then poured into water and extracted with ethyl acetate. The organic phase was dried and evaporated in a rotary evaporator. 0.79 g of 1-(4-aminophenyl)-4-(N-(4-aminobenzyl)-N-methylamino)piperidine was obtained Melting point 123° C.

PREPARATION 14

1.5 g (4.4 mmol) of the amine from Example 33 were dissolved in 100 ml of methanol and hydrogenated in the presence of 0.5 g of platinum/active carbon (5%). The mixture was then filtered and the filtrate was evaporated in a rotary evaporator. 1.1 g of 1-(4-aminophenyl)-4-(N-(4-fluorobenzyl)-N-methylamino)piperidine were obtained as an oil.

$^1$H NMR (d$_6$-DMSO): δ = 1.5–1.7 (2H), 1.8 (2H), 2.1 (3H), 2.35–2.6 (3H), 3.4 (2H), 3.55 (2H), 4.5–4.7 (2H), 6.5 (2H), 6.7 (2H), 7.1 (2H) and 7.35 (2H) ppm.

EXAMPLES

Example 1

3.3 g (16.2 mmol) of 1-(4-cyanophenyl)-4-piperidone, 1.0 g (16.2 mmol) of acetic acid and 4.0 g (32.4 mmol) of benzylmethylamine were dissolved in 50 ml of methanol, and 1.0 g (16.2 mmol) of sodium cyanoborohydride was added a little at a time. The mixture was stirred at room temperature for 2 h and then concentrated under reduced pressure, and the residue was partitioned between water and ethyl acetate. The organic phase was purified by chromatography (eluent: toluene/acetone 2:1), and ethereal hydrogen chloride solution was added in a conventional manner. 2.8 g of 1-(4-cyanophenyl)-4-(N-benzyl-N-methylamino)-piperidine dihydrochloride were obtained. Melting point 211°–212° C.

Example 2

1.5 g (25 mmol) of acetic acid and 1.6 g (25 mmol) of sodium cyanoborohydride were added successively to 5.0 g (25 mmol) of 1-(4-cyanophenyl)-4-pipe one and 4.5 g (25 mmol) of N-methyl-2-(4-nitrophenyl)ethylamine in 150 ml of methanol. The mixture was stirred at room temperature for 1 h and then the solvent was removed under reduced pressure. The residue was partitioned between dilute sodium hydroxide solution and ethyl acetate, and the organic phase was separated off, dried and concentrated under reduced pressure. The resulting oil was treated with ethereal hydrogen chloride solution in a conventional manner. 1-(4-Cyanophenyl)-4-(N- methyl-2-(4-nitrophenyl)ethylamino)piperidine dihydrochloride was obtained. Melting point 174°–178° C.

Example 3

1.2 g (3.3 mmol) of the product from Example 2 were hydrogenated on Pd/C (10%) in 100 ml of tetrahydrofuran and worked up in a conventional manner. 1.1 g of 4-(2-(4-aminophenyl)-N-methylethylamino)-1-(4-cyanophenyl)piperidine were obtained as an oil. $^1$H NMR (d$_6$-DMSO) $\delta = 1.2$–1.5 (2H); 1.8–1.9 (2H); 2.1 (3H); 2.4–2.7 (4H); 2.7–2.9 (2H); 3.3 (1H); 3.9 (2); 6.4 (2H); 6.8 (2H); 6.9 (2H) and 7.5 (2H) ppm.

Example 4

0.34 g (3 mmol) of methanesulfonyl chloride dissolved in tetrahydrofuran was added dropwise at 0° C. to 1.0 g (3 mmol) of the product from Example 3 and 0.6 g (6 mmol) of triethylamine in 100 ml of anhydrous tetrahydrofuran. The mixture was stirred at room temperature for 16 h and then the solvent was removed under reduced pressure. The residue was partitioned between aqueous sodium bicarbonate solution and methylene chloride, and the organic phase was dried and concentrated under reduced pressure. The resulting oil was purified by chromatography (eluent: methylene chloride/methanol 10:1). 0.73 g of 1-(4-cyanophenyl)-4-(2-(4-methanesulfonylaminophenyl)-N-methylethylamino) piperidine was obtained. $^1$H NMR (d-DMSO) $\delta = 1.3$–1.5 (2H); 1.7 (2H); 2.1 (3H); 2.5–2.7 (4H); 2.7–3.0 (5H); 3.3 (1H); 3.9 (2H); 6.9 (2H); 7.0–7.2 (4H); 7.5 (2H) and 9.6 (1H) ppm.

Example 5

2.5 g (11.4 mmol) of 1-(4-nitrophenyl)-4-piperidone, 1.5 g (11.4 mmol) of N-methyl-N-(2-phenylethyl)amine, 0.7 g (11.4 mmol) of acetic acid and 0.7 g (11.4 mmol) of sodium cyanoborohydride were reacted in a similar manner to Example 1. The product was converted into the fumarate with fumaric acid in a conventional manner. 2.8 g of 4-(N-methyl-N-(2-phenylethyl)amino)-1-(4-nitrophenyl)piperidine fumarate were obtained. Melting point 201°–202° C.

Example 6

1-(4-Nitrophenyl)-4-piperidone was reacted in a similar manner to Example 2 with N-benzyl-N-methylamine and then with fumaric acid. 4-(N-benzyl-N-methylamino)-1-(4-nitrophenyl)piperidine fumarate was obtained. Melting point 183° C.

Example 7

The product from Preparation 3 was reacted in a similar manner to Example 5 with N-benzyl-N-methylamine. 1-(4-Acetaminophenyl)-4-(N-benzyl-N-methylamino)piperidine was obtained. Melting point 147° C.

Example 8

5.5 g (16.3 mmol) of the product from Example 7 were refluxed in a mixture of 100 ml of 2M sodium hydroxide solution and 200 ml of methanol for 12 h. The reaction mixture was then concentrated under reduced pressure, the residue was partitioned between water and methylene chloride, and the organic phase was dried and concentrated under reduced pressure. 2.8 g of 1-(4-aminophenyl)-4-(N-benzyl-N-methylamino)piperidine were obtained as an oil which crystallized as difumarate. Melting point 138° C.

Example 9

The product from Example 8 was reacted in a similar manner to Example 4 with methanesulfonyl chloride and then converted into the hydrochloride. 4-(N-Benzyl-N-methylamino)-1-(4-methanesulfonylaminophenyl)piperidine dihydrochloride was obtained. Melting point 221° C. (decomposition).

Example 10

The product from Preparation 5 was reacted in a similar manner to Example 5 with N-methyl-N-(2-(4-nitrophenyl)ethyl)amine. 1-(4-Methanesulfonylaminophenyl)-4-(N-methyl-N-(2-(4-nitrophenyl)ethyl)amino)-piperidine was obtained. Melting point 225°–226° C.

Example 11

The product from Preparation 5 was reacted in a similar manner to Example 5 with N-methylpicolylamine. 1-(4-Methanesulfonylaminophenyl)-4-(N-methylpicolylamino)piperidine was obtained as an oil. $^1$H NMR (d$_6$-DMSO) $\delta = 1.4$–1.7 (2H); 1.7–1.9 (2H); 2.1 (3H); 2.4–2.7 (4H); 3.5–3.9 (3H); 6.9 (2H); 7.0 (2H); 7.3 (2H); 8.5 (2H); and 9.2 (1H) ppm.

Example 12

18.8 g (86 mmol) of the amine prepared in Preparation 9, 11.9 g (86 mmol) of 4-fluoroacetophenone and 47.5 g (344 mmol) of potassium carbonate in 250 ml of dimethylformamide were refluxed for 20 h. The mixture was then diluted with a large amount of water and extracted with ethyl acetate. The organic phase was dried and evaporated in a rotary evaporator. The residue was crystallized as the fumarate. 18.1 g of 1-(4-acetylphenyl)-4-(N-methyl-N-(2-phenylethyl)amino)-piperidine fumarate were obtained. Melting point 155°–157° C.

Example 13

10.4 g (0.32 mol) of the product from Example 12 (as base) were dissolved in 500 ml of methanol and, at 10° C., 18.0 g (0.475 mol) of sodium borohydride were added a little at a time. The mixture was stirred at room temperature for 16 hours and then evaporated in a rotary evaporator. The residue was partitioned between methylene chloride and water, and the organic phase was dried and evaporated in a rotary evaporator. The resulting oil was crystallized as the fumarate. 16.4 g of 1-(4-(1-hydroxyethyl)phenyl)-4-(N-methyl-N-(2-phenylethyl)amino)piperidine difumarate were obtained. Melting point 124°–129° C.

Example 14

A mixture of 5.1 g (15 mmol) of the product from Example 13, 2.6 g (22.5 mmol) of triethylsilane and 17.1 g (15 mmol) of trifluoroacetic acid was heated at 60° C. for 2 hours. The mixture was then poured into water, made alkaline with 4M sodium hydroxide solution and extracted with methylene chloride. The organic phase was separated off, dried and evaporated in a rotary evaporator. The resulting residue was purifed by chromatography on silica gel (eluent: toluene/acetone=2/1). The oily product crystallized as the fumarate. 1.5 g of 1-(4-ethylphenyl)-4-(N-methyl-N-(2-phenylethyl)amino)piperidine fumarate were obtained. Melting point 163°–165° C.

Example 15

4.0 g (20 mmol) of the product from Preparation 7, 3.1 g (20 mmol) of methyl 4-fluorobenzoate and 5.5 g (40 mmol) of potassium carbonate were reacted in a similar manner to Example 1. 2.1 g of 4-(N-benzyl-N-methylamino)-1-(4-methoxycarbonylphenyl)piperidine were obtained. Melting point 103°–104° C.

Example 16

4.5 g (13.2 mmol) of the product from Example 15 and 0.55 g of sodium hydroxide were dissolved in 150 ml of ethanol/water (1:1) and refluxed for 6 hours. The ethanol was then removed under reduced pressure, and the aqueous phase was neutralized with 1M hydrochloric acid, whereupon the product precipitated. 3.3 g of 4-(N-benzyl-N-methylaminio)-1-(4-carboxyphenyl)-piperidine were obtained. Melting point 227°–228° C.

Example 17

8.2 g (40 mmol) of the product from Preparation 7, 5.5 g (40 mmol) of 4-fluoroacetophenone and 11.0 g (40 mmol) of potassium carbonate were reacted in a similar manner to Example 12. 5.5 g of 1-(4-acetylphenyl)-4-(N-benzyl-N-methylamino)piperidine fumarate were obtained. Melting point: 163°–164° C.

Example 18

2.5 g (7.9 mmol) of the product from Example 17 were dissolved in 50 ml of glacial acetic acid and, at room temperature, 1.26 g (7.9 mmol) of bromine dissolved in 10 ml of glacial acetic acid were added dropwise. The mixture was stirred for 4 hours, after which ether was added, whereupon crystals slowly separated out. The crystals were filtered off and washed with ether. 3.5 g of 1-(4-acetyl-2-bromophenyl)-4-(N-benzyl-N-methylamino)piperidine hydrobromide were obtained. Melting point 201°–202° C.

Example 19

6.7 g (30 mmol) of the product from Preparation d11, 4.1 g (30 mmol) of 4-fluoroacetophenone and 8.3 g (60 mmol) of potassium carbonate were reacted in a similar manner to Example 12. 4.6 g of 1-(4-acetylphenyl)-4-(N-(4-fluorobenzyl)-N-methylamino)piperidine were obtained. Melting point 133° C.

Example 20

2.4 g (7 mmol) of the product from Example 19 were reduced with 2.4 g (20.9 mmol) of triethylsilane and 7.9 g (70 mmol) of glacial acetic acid in a similar manner to Example 14. 2.3 g of 1-(4-ethylphenyl)-4-(N-(4-fluorobenzyl)-N-methylamino)piperidine fumarate were obtained. Melting point 150°–152° C.

Example 21

8.2 g (40 mmol) of the product from Preparation 7, 5 g (40 mmol) of 4-fluorobenzaldehyde and 11.1 g (80 mmol) of potassium carbonate were reacted in a similar manner to Example 12. 8.4 g of 4-(N-benzyl-N-methylamino)-1-(4-formylphenyl)piperidine fumarate were obtained. Melting point 129°–133° C.

Example 22

1.5 g (5 mmol) of the product from Example 21 and 0.7 g (10 mmol) of hydroxylamine hydrochloride in 30 ml of ethanol were refluxed for 5 hours. On cooling, 1.2 g of 4-(N-benzyl-N-methylamino)-1-(4-(hydroxyiminomethyl)phenyl)piperidine hydrochloride crystallized. Melting point 238°–240° C.

Example 23

7.5 g (24 mmol) of the product from Example 21 were reduced with 1.0 g of sodium borohydride in a similar manner to Example 13. 4.1 g of 4-(N-benzyl-N-methylamino)-1-(4-(hydroxymethyl)phenyl)piperidine tartrate were obtained as an amorphous solid. $^1$H NMR (d$_6$-DMSO): δ=1.6–1.8 (2H), 1.9–2.0 (2H), 2.15 (3H), 2.5–2.7 (2H), 2.8 (1H), 2.7–2.9 (4H), 4.25 (2H; tartrate), 4.35 (2H), 6.0 (broad), 6.9 (2H), 7.2 (2H) and 7.3–7.5 (5H) ppm.

Example 24

1.9 g (6.1 mmol) of the base of the product from Example 23 were reduced with 1.1 g (9.2 mmol) of triethylsilane and 8.0 g of glacial acetic acid in a similar manner to Example 14. 2.0 g of 4-(N-benzyl-N-methylamino)-1-(4-tolyl)piperidine fumarate were obtained. Melting point 161°–163° C.

Example 25

6.7 g (30 mmol) of the amine from Preparation 11, 3.7 g (30 mmol) of 4-fluorobenzaldehyde and 8.3 g (60 mmol) of potassium carbonate were reacted in a similar manner to Example 12. 10.8 g of 4-(N-(4-fluorobenzyl)-N-methylamino)-1-(4-formylphenyl)piperidine fumarate were obtained. Melting point 114°–116° C.

Example 26

2.6 g (7.9 mmol) of the amine from Example 25 were reduced with 2.8 g (23.7 mmol) of triethylsilane and 9.0 g of trifluoroacetic acid in a similar manner to Example 14. 1.7 g of 4-(N-(4-fluorobenzyl)-N-methylamino)-1-(4-tolyl)piperidine fumarate were obtained. Melting point 146° C.

Example 27

9.3 g (60 mmol) of methyl 4-fluorobenzoate, 13.3 g (60 mmol) of the amine from Preparation 11 and 16.6 g (120 mmol) of potassium carbonate were reacted in a similar manner to Example 12. 8.4 g of 4-(N-(4-fluorobenzyl)-N-methylamino)-1-(4-methoxycarbonylphenyl)piperidine were obtained. Melting point 92° C.

Example 28

2.5 g (7 mmol) of the product from Example 27 in 140 ml of 1M sodium hydroxide solution/ethanol (1:1) were refluxed for 5 hours. The mixture was then worked up in a similar manner to Example 16. 1.8 g of 1-(4-carboxyphenyl)-4-(N-(4-fluorobenzyl)-N-methylamino)piperidine were obtained. Melting point: 256°–258° C.

Example 29

1.8 g (5.3 mmol) of the product from Example 28 were dissolved in 50 ml of methylene chloride, and 2.5 g (21.3 mmol) of thionyl chloride were added and the mixture was refluxed for 5 hours. The resulting solution was added dropwise to a vigorously stirred mixture of 100 ml of aqueous ammonia solution and 100 ml of methylene chloride at 0° C. The organic phase was then separated off, dried and evaporated in a rotary evaporator. The residue was purified by chromatography and crystallized as the tartrate. 0.4 g of 1-(4-carbamoylphenyl)-4-(N-(4-fluorobenzyl)-N-methylamino)piperidine tartrate was obtained. Melting point 204° C.

Example 30

Solution A: 2.6 g of copper(II) sulfate pentahydrate and 0.9 g of sodium chloride were dissolved in 8 ml of water, and to this was added a solution prepared from 0.65 g of sodium sulfite and 2 ml of water. A precipitate was dissolved in 4.1 ml of concentrated hydrochloric acid and added to the above solution.

2.3 g (7.7 mmol) of the amine from Example 8 were dissolved in 4.6 ml of 50% concentrated hydrochloric acid. The solution was cooled to below 5° C. and 3.1 ml of a 2.5M sodium nitrite solution were added dropwise. The resulting solution of the diazo compound was then added to solution A at 0° C., and the mixture was heated until nitrogen evolution ceased. The mixture was then poured into 2M sodium hydroxide solution. This aqueous phase was extracted with methylene chloride. The organic phase was separated off, dried and evaporated in a rotary evaporator. The resulting oil was crystallized as the fumarate. 1.1 g of 4-(N-benzyl-N-methylamino)-1-(4-chlorophenyl)piperidine fumarate were obtained. Melting point 151°-153° C.

Example 31

3.1 g (15 mmol) of the amine from Preparation 7, 2.5 g (15 mmol) of 4-fluorobenzotrifluoride and 4.2 g (30 mmol) of potassium carbonate were reacted in a similar manner to Example 12. 1.4 g of 4-(N-benzyl-N-methylamino)-1-(4-(trifluoromethyl)phenyl)piperidine fumarate were obtained. Melting point 162°-164° C.

Example 32

3.3 g (15 mmol) of the amine from Preparation 11, 1.8 g (15 mmol) of 4-fluorobenzonitrile and 4.2 g (30 mol) of potassium carbonate were reacted in a similar manner to Example 12. 2.95 g of 1-(4-cyanophenyl)-4-(N-(4-fluorobenzyl)-N-methylamino)piperidine were obtained. Melting point 100°-101° C.

Example 33

12.0 g (54 mmol) of the amine from Preparation 11, 7.6 g (54 mmol) of 4-fluoro-1-nitrobenzene and 7.5 g (54 mmol) of potassium carbonate were reacted in a similar manner to Example 12. 15.4 g of 4-(N-(4-fluorobenzyl)-N-methylamino)-1-(4-nitrophenyl)piperidine were obtained. Melting point 89°-90° C.

Example 34

4.3 g (15.0 mmol) of titanium(IV) isopropylate were added dropwise to 3.2 g (12.0 mmol) of the product from Preparation 5 and 2.0 g (12.0 mmol) of N-methyl-N-(p-nitrobenzyl)amine. After stirring at room temperature for 1 hour, 25 ml of anhydrous tetrahydrofuran were added. Subsequently 0.5 g (8.0 mmol) of sodium cyanoborohydride was added a little at a time, and the mixture was stirred for 3 hours. It was then hydrolyzed with 2.4 ml of water, the resulting precipitate was filtered off with suction, and the filtrate was extracted with methylene chloride. The organic phase was separated off, dried and evaporated in a rotary evaporator. 1.8 g of 1-(4-methanesulfonamidophenyl)-4-(N-methyl-N-(4-nitrobenzyl)amino)piperidine were obtained. Melting point 167°-168° C.

Example 35

4.0 (12.3 mmol) of the product from Preparation 12 and 1.92 ml (24.7 mmol) of methanesulfonyl chloride were reacted in a similar manner to Example 4. 1.2 g of 1-(4-methanesulfonamidophenyl)-4-(N-(2-(4-methanesulfonamidophenyl)ethyl)-N-methylamino)-piperidine were obtained. $^1$H NMR (d$_6$-DMSO): δ=1.3-1.5 (2H), 1.7-1.8 (2H), 2.3 (3H), 2.4-2.7 (7H), 2.85 (3H), 2.9 (3H), 3.6 (2H), 6.9 (2H), 7.0-7.3 (6H), 9.2 (1H) and 9.5 (1H).

2.7 g (12.3 mmol) of 1-(4-nitrophenyl)-4-piperidone and 2.0 g (12.3 mmol) of N-methyl-N-(4-n were reacted in a similar manner to Example 5. 3.0 g of 4-(N-methyl-N-(4-nitrobenzyl)amino)-1-(4-nitrophenyl)piperidine were obtained. Melting point 119°-120° C.

Example 37

4 0 g (12.9 mmol) of the product from Preparation 13 and 2.0 ml (12.9 mmol) of methanesulfonyl chloride were reacted in a similar manner to Example 4. 1.5 g of 1-(4-methanesulfonamidophenyl)-4-(N-(4-methanesulfonamidobenzyl)-N-methylamino)piperidine were obtained. Melting point 177°-179° C. $^1$H NMR (d$_6$-DMSO): δ=1.6 (2H), 1.8 (2H), 2.1 (3H), 2.5-2.7 (3H), 2.8 (3H), 2.9 (3H), 3.5 (2H), 3.7 (2H), 6.9 (2H), 7.1 (2H), 7.15 (2H), 7.25 (2H), 9.2 (1H) and 9.65 ($^1$H) ppm.

EXAMPLE 38

3.0 g (13.6 mmol) of 1-(4-nitrophenyl)-4-piperidone and 2.0 g (13.6 mmol) of N-(4-methoxybenzyl)-N-methylamine were reacted in a similar manner to Example 1. 3.5 g of 4-(N-(4-methoxybenzyl)-N-methylamino)-1-(4-nitrophenyl)piperidine were obtained. Melting point 144°-145° C.

Example 39

1.0 g (3.2 mmol) of the amine from Preparation 14 was diazotized in a similar manner to Example 30 and boiled with 0.28 g of sodium chloride. 0.8 g of 1-(4-chlorophenyl)-4-(N-(4-fluorobenzyl)-N-methylamino)-piperidine was obtained. Melting point 72°-73° C.

Example 40

2.4 g (10.9 mmol) of 1-(4-nitrophenyl)-4-piperidone and 2.0 g (10.9 mmol) of N-methyl-N-(2-(4-nitrophenyl)ethyl)amine were reacted in a similar manner to Example 1. 2.2 g of 1-(4-nitrophenyl)-4-(N-methyl-N-(2-(4-nitrophenyl)ethyl)amino)piperidine were obtained. Melting point 97°-98° C.

Antiarrhythmic Effect

The effect of the phenylpiperidylamines I as repolarization inhibitors can be demonstrated by ECG measurements. In these, the cardiac cycle is divided chronologically into systole (contraction of the heart), also called QT interval, and diastole (relaxation of the heart with filling of the ventricles with blood). Repolarization inhibitors increase the QT interval without causing a significant change in the atrioventricular conduction time (PQ interval) and the isometric contraction period (QRS time, from start of systole until the semilunar valves open).

The activity of the compounds according to the invention as repolarization inhibitors can be investigated in animal experiments by ECG measurements on, for example, the guinea pig heart (see Basic Res. Cardiol. 82 (1987) 437; J. Pharmacol. Methods 21 (1989) 195). In these, the activities of different substances are compared using, for example, the dose of an active ingredient which increases the QT interval by 20% (ED$_{20\%}$). For this, the logarithms of the doses of the relevant substances are plotted against the experimentally found relative changes in the QT interval, and linear regression is used to determine the equation for a straight line from which the $ED_{20\%}$ can then be calculated.

The experimental animals were male Duncin-Hartley guinea pigs with a body weight of 300 to 350 g. 30 min after administration of 1250 I.U. of heparin/kg of body weight into the abdominal cavity, the animals were sacrificed by a blow to the back of the neck. The carotid arteries were severed for exsanguination and then the thoracic cavity was opened, and the heart was dissected out and attached to a perfusion apparatus. Langendorff perfusion took place with oxygen-enriched Krebs-Henseleit solution (NaCl 6896 mg/l; KCl 350 mg/l; $MgSO_4$ 285 mg/l; $CaCl_2$ 370 mg/l; $KH_2PO_4$ 161 mg/l; $NaHCO_3$ 2090 mg/l; glucose 2000 mg/l) at 37° C. The perfusion volume per unit time was adjusted to 4 to 6 ml/min for a total volume of 100 ml, and the perfusion pressure was adjusted to 60 to 70 mm Hg. Equilibration for 30 minutes was followed by circulating perfusion.

The ECG measurements were recorded via two silver electrodes attached to the surface of the heart in the upper region of the left coronary artery and on the rear of the heart at the valve level. The PQ and QT intervals and QRS time, and the heart rate were measured.

The substance was administered cumulatively at intervals of 15 min into the perfusate. Binding to the sigma receptor The binding assay used (binding of [$^3$H]-ditolylguanidine) embraces the haloperidol-sensitive sigma receptors which have a high affinity for haloperidol but only low affinity for phencyclidine and for opioids. Methods:

α) Membrane Preparation

Rat cerebra were homogenized in 10 times the volume of homogenization buffer (50 mmol/1 tris(hydroxymethyl)aminomethane, 0.1 mmol/1 of ethylenediaminetetraacetate, pH=7.7) with a Polytron homogenizer (20 sec). The pellet obtained after centrifugation at 40,000 rpm for 15 min was resuspended, and the suspension was again centrifuged at 40,000 rpm for 15 min. The pellet resulting from this was resuspended in 5 times the volume of homogenization buffer and stored in liquid nitrogen until used.

β) Sigma Binding Assay

The test substance and membranes (0.3 mg of protein) were incubated in 0.3 ml of incubation buffer (5 mmol/1 tris(hydroxymethyl)aminomethane, 0.1 mmol/1 of ethylenediaminetetraacetate, pH=7.7) at 37° C. for 45 minutes. 100,000 dpm of [$^3$H]-ditolylguanidine (54.5 Ci/mmol) were added and the mixture was incubated for 1 hour. The membranes were removed on GF/B filters (dunn-Labortechnik, Asbach) and washed with washing buffer (5 mmol/1 tris(hydroxymethyl)aminomethane, 0.1 mmol/1 ethylenediaminetetraacetate, pH 7.4) at 37° C. The radioactivity remaining on the filters was measured by liquid scintillation counting. The binding data were analyzed by iterative curve-fitting programs. ATP-dependent K+ flux The ATP-dependent K+ flux (A. Noma, Nature 305 (1983) 147-148) was measured on isolated guinea pig ventricular myocytes using the patch clamp technique in the whole cell configuration (O. P. Hamill et al., Pflügers Arch. 391, (1981) 85-100). The I/V plot of the total K+ flux of the ventricular cells was recorded with voltages from −100 mV to 60 mV. The ATP-dependent K+ flux was activated either with dinitrophenol (W. J. Lederer et al., J. Physiol. (London) 413 (1989) 329-349) or with cromakalim (D. Escande et al., Biochem. Biophys. Res. Comm. 154 (1988) 620-625). A selective blocker for the ATP-dependent K flux in ventricular cells and β-cells is the sulfonylurea glibenclamide (S. J. H. Ashcroft et al., Cellular Signalling 2 (1990) 197-214).

We claim:

1. A phenylpiperidylamine of the formula I

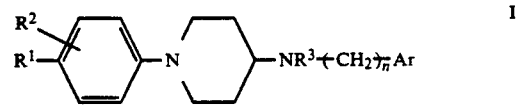

where
$R^1$ is H, $NO_2$, $R^4SO_2NH$,

N≡C, $CF_3$, $CF_3O$, F, Cl, Br, $C_1$-$C_4$-alkyl, $R^3O$, $CO_2R^3$, CHO, CH=$NOR^3$, $CH_3OR^3$ and
$R^2$ is H, F, Cl, Br, $C_1$-$C_4$-alkyl or $R^4O$, where $R^1$ and $R^2$ are not both H,
$R^3$ is H or $R^4$,
$R^4$ is $C_1$-$C_4$-alkyl or phenyl,
n is 1, 2, 3 or 4 and
Ar is

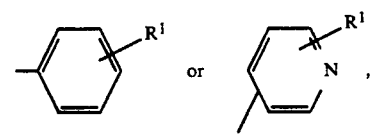

and the physiologically tolerated salts thereof.

2. A pharmaceutical composition which contains from 50 to 1,750 mg of a compound as claimed in claim 1 per dose as active ingredient in addition to pharmaceutically acceptable inert auxiliaries.

* * * * *